United States Patent
Riebel et al.

(10) Patent No.: US 6,202,494 B1
(45) Date of Patent: *Mar. 20, 2001

(54) PROCESS AND APPARATUS FOR MEASURING DENSITY AND MASS FLOW

(75) Inventors: Ulrich Riebel, Briesen; Peter Khatchikian, Cottbus, both of (DE)

(73) Assignee: Degussa-Huls Aktiengesellschaft (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/084,970

(22) Filed: May 28, 1998

(30) Foreign Application Priority Data

May 28, 1997 (DE) .............................. 197 22 274

(51) Int. Cl.$^7$ ....................................... G01F 1/74
(52) U.S. Cl. .......................................... 73/861.29
(58) Field of Search ................ 73/24.05, 24.03, 73/861.29, 861.28

(56) References Cited

U.S. PATENT DOCUMENTS

| | | | |
|---|---|---|---|
| 3,496,771 | * | 2/1970 | Moffatt ................................ 73/24.05 |
| 4,445,389 | * | 5/1984 | Potzick et al. .................... 73/861.28 |
| 4,542,644 | | 9/1985 | Shen . |
| 4,882,934 | | 11/1989 | Leffert et al. . |
| 5,035,147 | * | 7/1991 | Woodard .......................... 73/861.29 |
| 5,115,670 | | 5/1992 | Claytor et al. . |
| 5,159,843 | * | 11/1992 | Shakkottai et al. ................. 73/24.05 |
| 5,214,966 | | 6/1993 | Delsing . |
| 5,369,998 | * | 12/1994 | Sowerby ............................ 73/861.28 |
| 5,421,212 | * | 6/1995 | Nayranen et al. ................. 73/861.28 |
| 5,493,916 | * | 2/1996 | Bignell .............................. 73/861.28 |
| 5,717,145 | * | 2/1998 | Yasuhara et al. ................. 73/861.29 |

FOREIGN PATENT DOCUMENTS

| | | |
|---|---|---|
| 84 22 080 U | 1/1985 | (DE) . |
| 3825422 A1 | 2/1990 | (DE) . |
| 4237907 A1 | 5/1994 | (DE) . |
| WO91/09284 | 6/1991 | (WO) . |
| WO93/14382 | 7/1993 | (WO) . |

* cited by examiner

*Primary Examiner*—Robert Raevis
(74) *Attorney, Agent, or Firm*—Smith, Gambrell & Russell, LLP

(57) ABSTRACT

Measurement of density and mass flow of disperse systems with a gas as fluid phase flowing through a pipe is carried out by introducing sound in the frequency range 20–2,000 Hz in the middle of the cross-section of the pipe. The sound has a wavelength which is at least half the pipe diameter. The speed propagation of sound waves in the flowing disperse system is is measured in the axial direction of flow over at least two transit sections of differing length; and the speed propagation of sound waves in the flowing disperse system is also measured in a direction contrary to the axial direction of flow over at least two transit sections of differing length. The fill level of a reception member in communication with a line of the disperse system is calculated from the measured mass flow rate over a period of time.

2 Claims, 4 Drawing Sheets

Measuring arrangement with a sound source

FIG. 1

Caculated sonic speed as a function of the bulk density for an aerosol in air suspension, particle size ≈ 35 nm.

Variant with two transmitters for measurement on the same suspension segment

Possible pulse shape, f=500 Hz, 10 wave trains, Gaussian envelope curve, receiver spacing L=350 mm, signal transit time T = 5 ms.

PROCESS AND APPARATUS FOR MEASURING DENSITY AND MASS FLOW

FIELD OF THE INVENTION

The invention relates to a process and apparatus for measuring density and mass flow in respect to disperse systems with a gas as fluid phase.

KNOWN PROCESSES

Instruments for measuring mass flow in liquids and gases on the basis of a determination of the transit time of ultrasonic pulses are manufactured by, for example, Panametrics Ltd.

The book *Sensors* by Göpel W, Hesse J, Zemel J N, Volume 7 (Mechanical Sensors), published in 1993 by V C H Weinheim, ISBN 3-527-26773-5, contains a compilation of processes for measuring the most diverse physical magnitudes, inter alia also subject to the use of (ultra)sonic techniques. With a view to measuring density in multicomponent gases, attention is drawn to the possibility of calculating the density of the gas from the measured speed of sound.

With a view to measuring flow rate and mass flow, in water and other liquids for example, processes are described in which ultrasonic pulses are transmitted obliquely through a pipe having the liquid flowing through it. In a special application for refineries etc, streams of leaking gas in gas flows are identified by the change in molecular mass.

(Smalling J W, Braswell L D, Lynnworth L C, Wallace D R, Proc. 39th Annual Symp. on Instrumentation for the Process Industries, ISA (1984) 27–38, and Smalling J W, Braswell L D, Lynnworth L C and U.S. Pat. No. 4,596,133 (1986)).

SUMMARY OF THE INVENTION

The present invention provides a process and device for measuring density and mass flow in respect to disperse systems with a gas as fluid phase, said device being characterized in that the speed of propagation of sound waves (sonic speed) is measured in the flowing disperse system both in the direction of flow and contrary to the direction of flow.

The sound waves may be used in the form of continuous sound or in the form of sonic pulses. Prior to further describing the present invention, some additional physical background discussion is provided.

1. Physical Background 1.1. Measuring the Suspension Density

In pure gases the speed of sound depends exclusively on the density and the compressibility of the medium. For instance, in air the following holds:

$$c_L = \sqrt{\frac{1}{K_L \cdot P_L}} \quad (1)$$

with $c_L$=speed of sound in air [m/s], $K_L$=compressibility of air [m$^2$/N] and $P_L$=density of air [kg/m$^3$]. In disperse systems the speed of sound is generally strongly dependent on the wavelength of the sound and on the size of the dispersed particles. However, if the particles are very much smaller than the wavelength, with respect to the propagation of sound the suspension behaves like a homogeneous system and Equation (1) applies accordingly. Mean values of the two phases then have to be used for the density and compressibility, i.e.

$$C_{susp} = \sqrt{\frac{1}{K \cdot P}} \quad (2)$$

$$K = (1-C_V) \cdot K_L + C_V \cdot K_P \quad (3)$$

$$P = (1-C_V) \cdot P_L + C_V \cdot P_P \quad (4)$$

$C_V$: volumetric concentration [m$^3$/m$^3$]
L: air; P: particles

If the speed of sound in such a suspension is measured, then from Equations (2) to (4) the volumetric concentration of the particles can be derived by calculation. In turn, the bulk density or transport density can easily be determined from this result. FIG. 1 shows the sonic speed as calculated by Equation (2) plotted against the bulk density. For still higher values of the bulk density the sonic speed would again rise. If the density is able to assume such large values the unambiguous correspondence of a measured value of c to a bulk density is not possible. In the case of light bulk materials such as precipitated silicas (e.g. AEROSIL® precipitated silicas of Degussa Aktiengesellschaft) or carbon black, as a matter of principle the monotonously falling region of the curve applies.

Of course, a check has to be made as to whether the particles are sufficiently small in relation to the wavelength. The sound wave represents a vibration of the air which is transmitted more or less intensely to the particles. The stated assumption of a homogeneous medium then applies if the particles are fully able to conform to the vibration of the air—i.e. if their oscillation amplitude is exactly the same as that of the air. For the ratio of the two amplitudes, Skudrzyk in his book *Grundlagen der Akustik* (Springer Verlag 1954) states a relationship which can be solved for the sound frequency. If, arbitrarily, an amplitude ratio=0.99 is required, a sound frequency of f=2.5 MHz for a particle size of 35 nm AEROSIL® material results in this case.

One objective of the present invention is to make use of Eqn. (2) for a range of particle sizes that is as broad as possible and the invention therefore provides for measuring at frequencies that lie far below this limit, to be specific preferably in the range 20–2,000 Hz, in particular 105 to 2,000 Hz. In this frequency range the attenuation of the sound is also very slight, so that a particularly precise measurement appears to be possible through the choice of a very long measuring length.

However, macroscopic inhomogeneities in the suspension, such as large agglomerates for example, may constitute a problem. Such regions of relatively high bulk density are then no longer much smaller than the wavelength and they result in a frequency dependency of the speed of sound. But the errors arising as a result can be compensated by empirical calibration.

Another criterion to be taken into account, in accordance with the invention, in the choice of the measuring frequency is the diameter of the pipeline on which the measurement is to be carried out.

If an embodiment of the process is chosen in which the propagation of the sound is measured lengthwise in relation to the pipe axis then wave portions radiated obliquely may reach the receiver as a result of multiple reflection on the pipe wall, be superimposed with the waves transmitted directly and falsify the result.

In a preferred embodiment of the invention it is therefore stipulated that the frequency of the sound be chosen so as to result in a wavelength that is at least equal to one half of the diameter of the pipe. For such waves and longer waves, propagation is only possible in the direction of the pipe axis and the error is avoided.

On the other hand it has to be taken into consideration that the material oscillating with the sound wave experiences friction on the pipe wall, said friction being dependent on the condition of the pipe surface. This friction also results in a change in the speed of sound propagation which cannot be calculated in advance and which may also change in time-dependent manner, for example as a result of corrosion. The influence of the wall makes itself felt above all when the wavelength becomes clearly longer than the diameter of the pipe.

Therefore, in a preferred embodiment of the present invention, the wavelength should be between one half and 10 times the diameter of the pipe.

1.2 Measuring the Flow Velocity and the Mass Flow

If a sound wave is propagated in a flowing suspension in the same direction as the flow ('with the flow'), a static observer sees a sonic speed that is increased by the flow velocity. In the case of propagation contrary to the flow the measurable value is correspondingly smaller. With a view to simultaneous measurement of suspension density and flow rate the two sonic speeds have to be measured with the direction of flow and contrary to the direction of flow as simultaneously as possible. The techniques for measuring the sonic speed are elucidated in more detail in the following section; as a rule it is the measurement of the time T needed by the wave in order to traverse the known distance L. Given the sonic speed c of the motionless suspension and the flow rate v, the distance-time law for propagation with the flow is $$c + v = \frac{L}{T_{with}} \quad (5)$$

and for propagation contrary to the flow it is $$c - v = \frac{L}{T_{contr}} \quad (6)$$

From these two equations the conditional equations follow for the two magnitudes being sought:

$$v = \frac{L}{2}\left[\frac{1}{T_{with}} - \frac{1}{T_{contr}}\right] \quad (7)$$

and $$c = \frac{L}{2}\left[\frac{1}{T_{with}} + \frac{1}{T_{contr}}\right]. \quad (8)$$

Given the cross-sectional area A of the pipe, the mass flow is then finally $$m = P \cdot v \cdot A \quad (9)$$

A practical numerical example may serve to illustrate the measuring concept:
Bulk density in the pipe: P=30 g/l;
Sonic speed: c=70 m/s; (from FIG. 1)
Conveying speed: v=3 m/s;
Receiver spacing: L=300 mm.
The following should then be measured:
Signal transit times:
  $T_{with}$=4.11 ms;
  $T_{contr}$=4.48 ms.

Equation (8) then determines the bulk density on the basis of the mean value of the two sonic speeds. But the difference of the two values, which are relatively close together, enters into Equation (7). These therefore have to be measured very precisely, it then being possible for the random error to be reduced by averaging several measured transit times.

Errors may also arise in particular when the transit times $T_{with}$ and $T_{contr}$ are measured at different times and when the density of the bulk material has changed in the meantime. A particularly advantageous embodiment of the invention therefore provides for measuring both transit times at precisely the same time.

A further subject of the invention is a device for measuring density and mass flow in respect of disperse systems with a gas as fluid phase, said device being characterised in that a sound source (sonic transducer) and, at a distance from the sound source, various, at least two, sonic receiver-transducers are arranged on a line conducting the disperse system.

BRIEF DESCRIPTION OF THE DRAWINGS

FIG. 1 shows a graph of calculated sonic speed versus bulk density for AEROSIL® MATERIAL;

DETAILED DESCRIPTION OF THE PREFERRED EMBODIMENTS OF THE INVENTION

Figure 2:
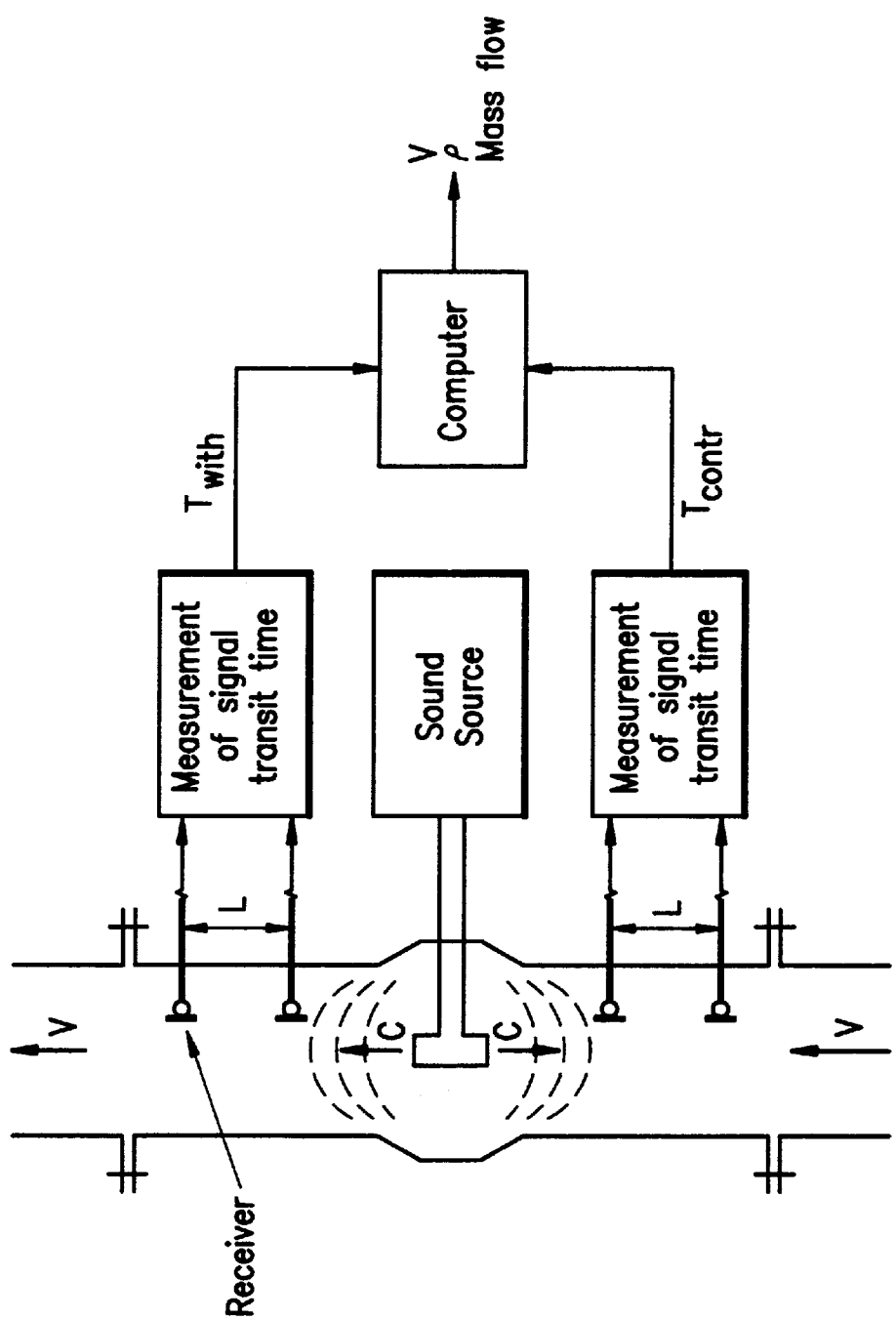
FIG. 2 shows a first embodiment of a measuring device of the present invention positioned in a dispersed system line.

One possible arrangement for measuring the sonic speed is shown in FIG. 2. A signal generator generates the sonic pulses firstly as an electrical signal. The latter is converted by a sonic transducer (in the simplest case an ordinary loudspeaker) into a sound wave and is introduced into the suspension in such a way that the wave is propagated simultaneously with the direction of flow and contrary to the direction of flow. The sonic receiver-transducers (microphones or pressure gauges) convert the sound wave back into electrical signals. A pair of receivers is provided both upstream and downstream. The two receivers located downstream see, for example, the same signal which, however, is shifted by the signal transit time $T_{with}$. The two transit times $T_{with}$ and $T_{contr}$ are measured automatically and utilised in accordance with Equations (7) to (8) in order to calculate the magnitudes being sought.

Since in the event of fluctuations in concentration the sonic speed and sonic attenuation are highly variable, it can be advantageous to use more than two receivers for each transit direction (e.g. one or more additional receivers in series or radially spaced from the receivers illustrated), in order to be able to select, from the various signals received, the optimal signal for the evaluation and in order in the event of measurements with continuous sound to be able to determine the phase position of the wave unambiguously.

Figure 3:
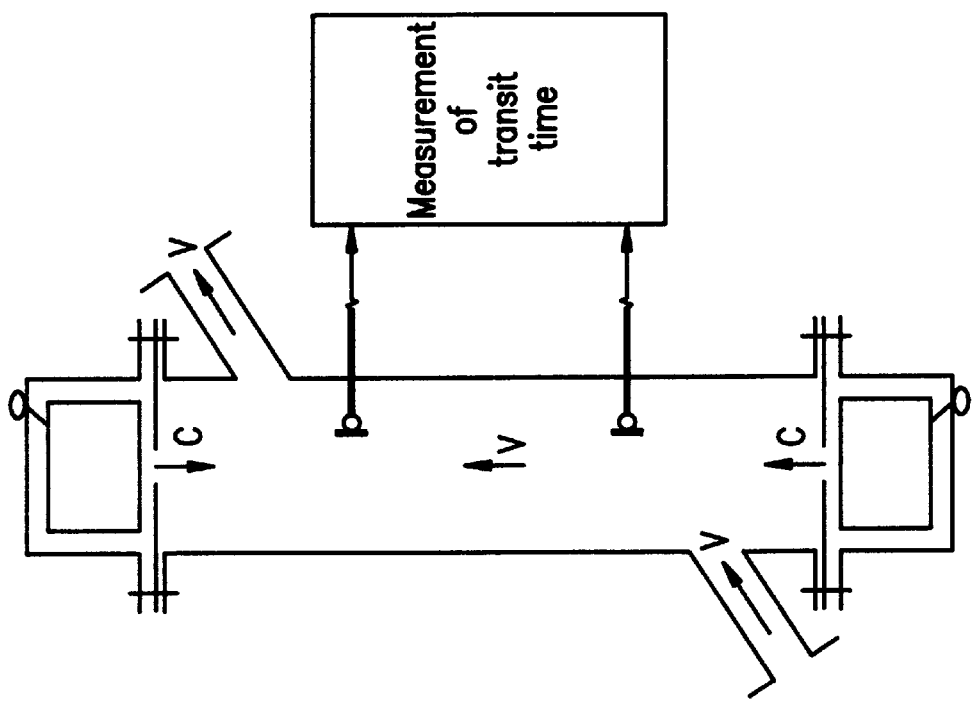
FIG. 3 shows another embodiment of a measuring device of the present invention.

Another arrangement, which is represented in FIG. 3, differs in a few details from the first arrangement. It makes do with only two receivers, but, here too, devices with several receivers are useful. For this purpose two transmitters are provided which emit pulses alternately or simultaneously. If they operate synchronously, the measured transit times relate to exactly the same segment of the suspension.

As a result, random inhomogeneities, such as air bubbles for example, cause smaller errors in the flow-rate measurement. On the other hand, the main current has to be deflected.

In addition to the two arrangements shown, quite a few other arrangements are of course conceivable which have advantages and disadvantages with respect to the measuring process but also with regard to disturbance of the flow of material.

Measurement of the Signal Transit Time

The arrival of a sonic pulse is registered in many cases by the time being measured at which the signal emitted by the sensor exceeds a certain level. However, this process is very imprecise, particularly if the signal is overlaid by noise or the attenuation of the signal in the measuring length is temporally variable. In addition, by means of this process it is not the (theoretically calculable) phase velocity, see eqs. 2 to 4, which is measured but the group velocity, which differs from the phase velocity and which cannot readily be calculated theoretically. An advantageous configuration of the invention therefore provides for the phase velocity to be ascertained with the aid of the correlation function from the sonic signals which are to be registered digitally. Calculation of the cross-correlation function of the two signals suggests itself for automatic determination of the signal transit time between two receivers. This mathematical operation identifies any possible similarity of two signals and can also classify the type of this similarity to a certain extent. With the arrangements described above, the signals at two receivers are exactly equal in the ideal case but shifted by the transit time $T_{with}$ or $T_{contr}$. The cross-correlation function provides these transit times and is at the same time totally insensitive to disturbing influences such as signal amplitude variations or noise. On the other hand there are problems if the two signals to be correlated have different frequency spectra. The choice of the shape of the signal is therefore of particular importance.

Signals

As already explained, the speed of sound in bulk materials may depend on the frequency. For the process according to the invention it follows that the signals transmitted upstream and downstream must have the same frequency, since the transit-time difference that otherwise arises cannot be distinguished from the sometimes very small transit-time difference caused by the flow velocity. In order to compensate for this frequency influence in the determination of density, in addition to the empirical calibration there is also the possibility of measuring at different frequencies and averaging the results.

As a matter of principle a distinction has to be made between continuous sound and sonic pulses by way of signal. From the physical point of view the sinusoidal continuous sound is optimal, since it is spectrally pure and consequently contains only a single frequency component. Problematic in this connection is the unambiguous ascertainment of the signal transit time from the phase of the signal received if the receiver spacing is greater than one wavelength. The principal disadvantage, however, consists in the fact that the wave that is reflected on pipe elbows etc is superimposed on the transmitted wave and changes the phase thereof. Measurement of the sonic speed is then more elaborate.

In the case of pulsed sound it is possible in principle to distinguish the transmitted (desired) pulse from the reflected pulse and to evaluate only the desired pulse.

For these reasons, pulsed operation is preferred. But it should be clearly pointed out that the conditions in the case of the process according to the invention are different from those in the case of known ultrasonic applications. For instance, the wavelengths are much longer. The consequence of this is that, firstly, the receiver spacing can be kept smaller than one wavelength and, secondly, the reflected pulses cannot as a matter of principle be temporally separated from the transmitted pulses, so that this advantage of pulsed insonification does not always fully come to bear.

Figure 4:
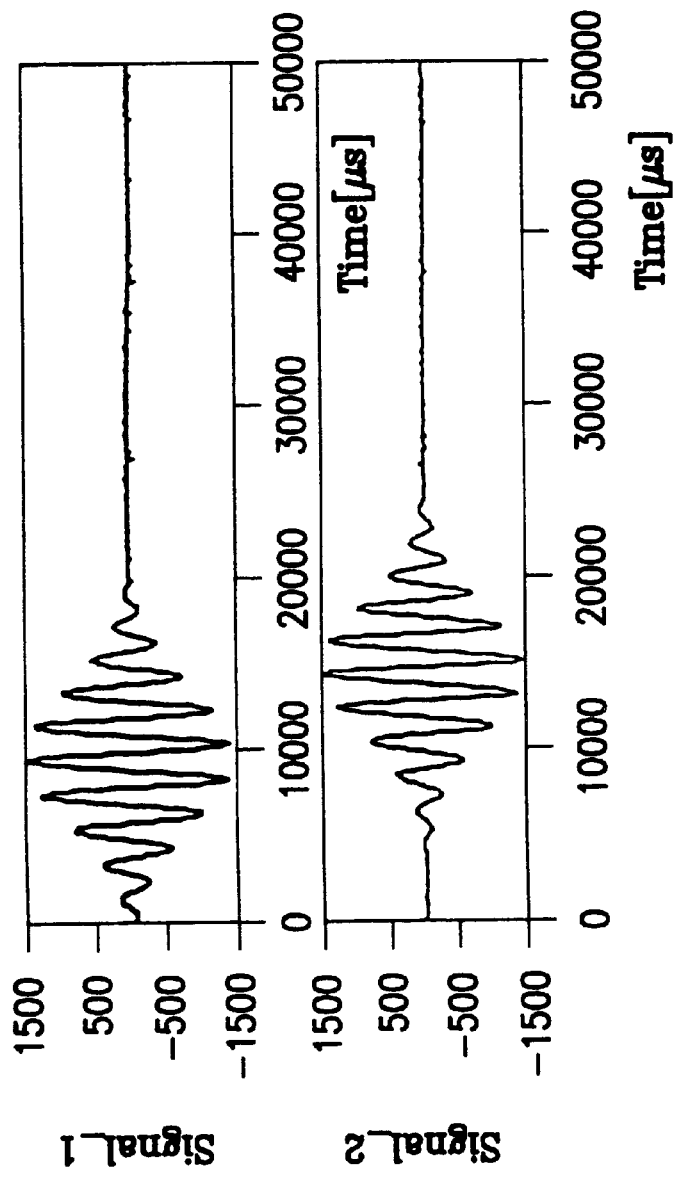
FIG. 4 shows one possible pulse shape such as would be received in sequence by two receivers.

FIG. 4 shows one possible pulse shape such as would be received in sequence by two receivers. Such a pulse may be described as the product of an envelope curve with a sinusoidal carrier oscillation, that is to say, $I(t)=H(t)*\sin(2\pi f*t)$. Here f is designated as the carrier frequency.

A disadvantage of the pulse generally is its spectral width—i.e. the portion of the signal power having a frequency different from f. Since the portions of the pulse of different frequency propagate at different speeds, the pulse changes its shape on passing through the suspension, to be specific, the more so the further it has travelled. This complicates the calculation of the transit time with the cross-correlation function, since signals then have to be correlated that differ not only by virtue of a shift on the time axis. For a given carrier frequency and number of wave trains the envelope curve alone determines the extent of spectral widening. The Gaussian bell-shaped curve of FIG. 4 is optimal in this respect—that is to say, a pulse signal with a Gaussian envelope curve produces, for a given pulse width, the narrowest frequency spectrum and the lowest possible dispersion.

Another possibility for improving the spectral purity is to increase the number of wave trains in the pulse. However, with a constant carrier frequency the pulse would then become too long and the reflection problems would be intensified. If the frequency is increased, the attenuation in the suspension, which increases with the square of f, becomes too high.

With an arrangement according to FIG. 3 it is conceivable to transmit two slightly different pulses at precisely the same time. In this case the superposition of the two signals is not inconvenient, although they cannot be temporally separated.

Moreover, use could be made of an intentionally broadband pulse. The measured sonic speed then represents a mean value over a wide frequency band. The possibility of generating such a simple signal without a sonic transducer in the narrower sense, for example by means of an impact using a hammer etc, appears to be attractive.

By way of continuous variant of the broadband pulse a similarly broadband noise (noise signal) enters into consideration.

Noise signals have the advantage that two signals generated independently of one another can be unambiguously distinguished from one another despite having the same frequency spectrum. Accordingly, if two independent noise signals are transmitted and evaluated with the correlation process then measurements can be carried out simultaneously and continuously in the same measuring length in both directions of propagation. This embodiment is particularly advantageous when the material shows only slight dispersion, that is to say, in the case of very fine, homogeneous bulk materials.

Both variants have the decisive advantage that, given a suitable choice of the receiver spacing, they can be made insensitive to the influence of the reflected waves. For, in contrast with narrowband signals, it is possible for the two portions to be distinguished on the basis of the cross-correlation function.

In one embodiment of the invention the sound waves (autogenous sound waves) generated by turbulences of the flow itself may be utilised. In another embodiment of the invention the influence of the wave portions reflected outside the measuring length which falsify the measurement can be eliminated, to be specific either by means of a sound-muffling configuration of the pipe outside the measuring length or by means of a controlled antiphase sonic pulse which prevents emergence of the sound waves from the region of the measuring length.

The process according to the invention is suitable for measuring the overall density, the flow rate and also the mass flow of a flowing, disperse system. If the measured mass flow is integrated over time, then the filling level of a charged silo, for example, can be predicted for monitoring purposes. The main application might well be the pneumatic transport of fine bulk materials such as, for example, carbon black, pyrogenically produced silicas or other highly dispersed solids. Also conceivable is, for example, measurement of the recirculation in the case of circulating fluidised beds or only of the bulk density in the case of a stationary fluidised bed.

Other applications relate to the measurement of foams and all flows containing bubbles in which the speed of sound can be calculated similarly in accordance with Equation (2).

DE 19722274.9 filed May 28, 1997 in Germany is herein incorporated by reference in its entirety.

What is claimed is:

1. A device for measuring density and mass flow of a disperse system with a gas as fluid phase, flowing through a pipe which has a cross-section and a diameter, said device comprising:

a signal generator for generating an electrical signal;

a sonic transducer for converting the electrical signal into a sound wave which is propagated simultaneously in both the direction of flow and against the direction of flow;

said sound wave including sound in the frequency range of 20–2,000 Hz in the middle of the cross-section of the pipe, said sound wave having a wavelength which is at least half the magnitude of the diameter of the pipe, said sound wave being a pulsed sound which is the product of an envelope curve and a sinusoidal carrier oscillation having the formula $I(t)=H(t)*sin(2\pi f*t)$;

two sonic receivers, one located upstream of said sonic transducer and one located downstream of said sonic transducer, said two receivers being at different distances from said sonic transducer;

first means for measuring the speed propagation of sound waves in the flowing disperse system in the axial direction of flow;

second means for measuring the speed propagation of sound waves in the flowing disperse system in a direction against the axial direction of flow;

said first and second means for measuring the speed propagation producing a cross-correlation function of two signals to provide transit times and at the same time being totally insensitive to disturbing influences;

means for calculating a fill level based on the measured mass flow rate over a time period.

2. A process for measuring density and mass flow of a dispersed system with a gas as fluid phase, flowing through a pipe which has a cross-section and a diameter, said process comprising the steps of:

providing a signal generator for generating an electrical signal;

providing a sonic transducer for converting the electrical signal into a sound wave which is introduced into said gas by being propagated simultaneously both in the direction of flow and against the direction of flow, said sound wave including sound in the frequency range of 20–2,000 Hz in the middle of the cross-section of the pipe, said sound wave having a wavelength which is at least half the magnitude of the diameter of the pipe, said sound wave being a pulsed sound which is the product of an envelope curve and a sinusoidal carrier oscillation having the formula $I(t)=H(t)*sin(2\pi f*t)$;

providing two sonic receivers for converting said sound wave into electrical signals with one receiver being upstream of said sonic transducer and the other receiver being downstream of said sonic transducer, the distances between said receivers and said transducer being different;

measuring the speed propagation of sound waves in the flowing disperse system in the axial direction of flow;

measuring the speed propagation of sound waves in the flowing disperse system in a direction against the axial direction of flow;

producing a cross-correlation function; and calculating a fill level based on the measured mass flow rate over a time period.

* * * * *